United States Patent [19]
Funae et al.

[11] Patent Number: 6,068,920
[45] Date of Patent: May 30, 2000

[54] RANDOM-BLOCK COPOLYMER AND MONOFILAMENT THEREOF

[75] Inventors: Akihiro Funae; Kouichi Uchiki; Hideyuki Akieda; Yuzo Ono, all of Aichi-ken, Japan

[73] Assignee: Mitsui Chemicals, Inc., Japan

[21] Appl. No.: 09/136,515

[22] Filed: Aug. 19, 1998

[30] Foreign Application Priority Data

Sep. 4, 1997 [JP] Japan .................................... 9-256017
Oct. 16, 1997 [JP] Japan .................................... 9-283559

[51] Int. Cl.$^7$ ...................................................... A61L 17/12
[52] U.S. Cl. .......................... 428/401; 606/230; 528/354; 525/411; 525/415
[58] Field of Search .................................... 525/411, 415; 528/354; 428/401; 606/230

[56] References Cited

U.S. PATENT DOCUMENTS

| | | |
|---|---|---|
| 3,839,297 | 10/1974 | Wasserman et al. . |
| 4,052,988 | 10/1977 | Doddi et al. . |
| 4,243,775 | 1/1981 | Rosensaft et al. . |
| 4,605,730 | 8/1986 | Shalaby et al. . |
| 5,007,923 | 4/1991 | Bezwada et al. . |

FOREIGN PATENT DOCUMENTS

| | | |
|---|---|---|
| 441322 | 8/1991 | European Pat. Off. . |
| 761712 | 3/1997 | European Pat. Off. . |
| WO97/15609 | 5/1997 | WIPO . |

OTHER PUBLICATIONS

H.R. Kricheldorf et al, "Polylactones 3. Copolymerization of Glycolide with L,L–Lactide and Other Lactones", Makromolekulare Chemie, Macromolecular Chemistry and Physics, Supplements., vol. 12, 1985, pp. 25–38, XP002088422, Basel CH.

*Primary Examiner*—Patricia A. Short
*Attorney, Agent, or Firm*—Burns, Doane, Swecker & Mathis, L.L.P.

[57] ABSTRACT

A random-block copolymer having appropriate hydrolyzability, excellent flexibility and excellent mechanical strength, a monofilament thereof, and a process for producing the copolymer. The random-block copolymer comprises from 5 to 50 mol % of a random copolymer segment containing from 20 to 80 mol % of a lactide unit (A) and from 80 to 20 mol % of a caprolactone unit (B), and from 95 to 50 mol % of a block copolymer segment containing a glycolide unit (C).

6 Claims, No Drawings

RANDOM-BLOCK COPOLYMER AND MONOFILAMENT THEREOF

BACKGROUND OF THE INVENTION

1. Field of the Invention

The present invention relates to a random-block copolymer, a process for producing the same and a monofilament formed of this random-block copolymer. More specifically, the present invention relates to a random-block copolymer comprising a random copolymer segment containing a lactide unit and a caprolactone unit and a block copolymer segment containing a glycolide unit, a process for producing the same, and a monofilament which is formed of the random-block copolymer and which is appropriately used as a surgical suture.

2. Description of the Prior Art

As a random-block copolymer, polyglycolic acid (or polyglycolide), polylactic acid (or polylactide), polycaprolactone, poly(p-dioxanone). poly(trimethylene carbonate) and a copolymer thereof are known.

A multifilament suture produced from polyglycolic acid or a glycolide-lactide copolymer is in the form of a twisted yarn for providing a flexibility and a strength required because its material has a high rigidity. For this reason, bacteria tend to adhere to its surface. Further, since the filament is hard, a coating layer has to be formed on the surface to improve a tie down property. Accordingly, there is a problem that the production step becomes intricate (Japanese Patent Laid-Open No. 62,899/1973, U.S. Ser. No. 200,706).

In order to solve these drawbacks, Doddi et al produce a bioabsorbable monofilament from poly(p-dioxanone) and propose a suture which is as good as a twisted multifilament with respect to flexibility and strength (Japanese Patent Publication No. 36,785/1985, U.S. Pat. No. 4,052,988). The monofilament formed of poly(p-dioxanone) is indeed good in flexibility and strength, but has a low rate of hydrolysis. Accordingly, this monofilament is problematic in that it remains within the body for a long period of time.

Then, Bezwada et al disclose a bioabsorbable monofilament obtained from a random-block copolymer comprising a random copolymer segment of lactide and glycolide and a block polymer segment of p-dioxanone to improve flexibility, strength and further hydrolyzability of a monofilament made of poly(p-dioxanone) [Japanese Patent Laid-Open No.212,366/1992, U.S. Pat. No. 5,007,923]. It is however found that this random-block copolymer is improved in a flexibility (Young's modulus) and tensile strength but shows too high rate of hydrolysis in comparison with a monofilament formed of poly(p-dioxanone).

Further, Bezwada et al disclose a method in which a random copolymer of ε-caprolactone and glycolide is formed, and glycolide is further block-polymerized therewith to obtain a random-block copolymer (Japanese Patent Laid-Open No. 269,013/1991, U.S. Pat. No. 4,605,730). However, when the present inventors evaluated properties and the like thereof, it was found that the random-block copolymer of ε-caprolactone and glycolide has also a markedly high rate of hydrolysis.

Still further, Japanese Patent Laid-Open No. 132,638/1997 (EP-A-761712) discloses a three-component block copolymer comprising a polylactic acid segment, a poly(ε-caprolactone) segment and a glycolic acid segment, obtained by first subjecting from 20 to 1,200 parts by weight of ε-caprolactone to ring-opening polymerization in the presence of 100 parts by weight of polylactic acid containing a terminal hydroxyl group and having a weight average molecular weight of at least 2,000 and at most 500,000 and then adding from 15 to 1,200 parts by weight of glycolide during, or after the completion of, the ring-opening polymerization of the ε-caprolactone to conduct the ring-opening polymerization, this copolymer having a weight average molecular weight of from 10,000 to 1,000,000. A monofilament obtained from this three-component block copolymer has excellent strength, but is not yet satisfactory with respect to flexibility.

SUMMARY OF THE INVENTION

It is an object of the present invention to provide a random-block copolymer and a monofilament thereof which have a higher rate of hydrolysis than poly(p-dioxanone), which are more improved in flexibility and mechanical strength than a random-block copolymer comprising a random copolymer segment of lactide and glycolide and a block polymer segment of p-dioxanone and a monofilament thereof or a random-block copolymer comprising a random copolymer segment of ε-caprolactone and glycolide and a block polymer segment of glycolide and a monofilament thereof and which have further an appropriate rate of hydrolysis, and a process for producing the random-block copolymer.

The present inventors have assiduously conducted investigations, and have consequently found that a random-block copolymer comprising a random copolymer segment containing a lactide unit (A) and a caprolactone unit (B) and a block polymer segment containing a glycolide unit (C) in specific proportions provides a monofilament having appropriate flexibility, appropriate hydrolyzability and excellent mechanical strength.

The present invention relates to a random-block copolymer comprising from 5 to 50 mol % of a random copolymer segment containing from 20 to 80 mol % of a lactide unit (A) and from 80 to 20 mol % of a caprolactone unit (B), and from 95 to 50 mol % of a block polymer segment containing a glycolide unit (C).

Further, the present invention relates to a process for producing the above-mentioned random-block copolymer, which comprises random-copolymerizing from 20 to 80 mol % of lactide with from 80 to 20 mol % of caprolactone at from 140 to 200° C. in the presence of a catalyst and an initiator, and then adding from 95 to 50 mol % of glycolide to from 5 to 50 mol % of the resulting random copolymer to conduct block polymerization at from 180 to 240° C.

Still further, the present invention relates to a monofilament which is formed by spinning and stretching the above-mentioned random-block copolymer.

The random-block copolymer of the present invention has a higher rate of hydrolysis than a known hydrolyzable polyester, for example, poly(p-dioxanone). Further, it has a lower rate of hydrolysis, is richer in flexibility and has a better mechanical strength than a random-block copolymer comprising a random copolymer segment of lactide and glycolide and a block polymer segment of p-dioxanone or a random-block copolymer comprising a random copolymer segment of ε-caprolactone and glycolide and a block polymer segment of glycolide. That is, it has an appropriate rate of hydrolysis, appropriate mechanical strength and further excellent flexibility. Accordingly, when the random-block copolymer of the present invention is used, it can provide a bioabsorbable surgical suture which is not in the multifilament form but in the monofilament form.

The random-block copolymer of the present invention is produced by random-copolymerizing lactide and caprolactone in specific amounts in the presence of a catalyst and an initiator, and block-polymerizing the resulting random copolymer with a specific amount of glycolide.

Examples of the catalyst include tin chloride, tin oxide, tin fluoride, tetraphenyltin, stannous octoate, tin acetate, tin stearate, analogues thereof lead oxide, zinc oxide, boron trifluoride, antimony trifluoride, lead stearate, triethylamine, tributylamine, tributylphosphine and analogues thereof. Of these, stannous octoate which is approved in FDA, U.S.A. as a nontoxic stabilizer is preferable. The amount of the catalyst is preferably in the range of from 0.001 to 0.05 mol % based on the total amount of monomers which will be described later.

Examples of the initiator include an aliphatic alcohol, a glycol, a hydroxy acid and an amine. Specific examples thereof include aliphatic saturated alcohols such as methanol, ethanol, propanol, butanol, amyl alcohol, capryl alcohol and lauryl alcohol; alicyclic alcohols such as cyclopentanol and cyclohexanol; unsaturated alcohols; glycols such as diethylene glycol; hydroxycarboxylic acids such as lactic acid and glycolic acid; and amines such as aminophenol and acetaminophenone. Of these, lauryl alcohol is preferable. The amount of the initiator is preferably in the range of from 0.01 to 0.5 mol % based on the total amount of monomers which will be described later.

The monomers to be used are lactide, caprolactone and glycolide. When producing a lactide-caprolactone random copolymer, from 20 to 80 mol % of lactide are random-copolymerized with from 80 to 20 mol % of caprolactone in the presence of the above-mentioned catalyst and initiator. The polymerization temperature is between 140 and 200° C., preferably between 160 and 180° C. It is recommendable that the polymerization reaction is continued until the conversion of the monomers reaches at least 90% by weight, preferably at least 98% by weight. The polymerization time varies depending on the temperature, the amount of the catalyst and the amount of the initiator. It is preferably between 3 and 24 hours, more preferably between 6 and 12 hours. When it is less than 3 hours, the desired conversion is not reached at times. When it exceeds 24 hours, decomposition of the random copolymer occurs. Consequently, the molecular weight is decreased, and it is sometimes difficult to obtain a monofilament having desired properties.

Subsequently, from 95 to 50 mol % of glycolide is added to from 5 to 50 mol % of the resulting random copolymer, and the block polymerization is carried out at a temperature of from 180 to 240° C., preferably from 200 to 235° C. It is recommendable that the polymerization reaction is continued until the amount of the monomer reaches at least 80% by weight, preferably at least 98% by weight. After the completion of the polymerization reaction, it is recommendable that vacuum degassing is conducted at a pressure of 700 Pa (5 mmHg) or less in the above-mentioned temperature range as required. The polymerization time varies depending on the temperature and the amounts of the catalyst and the initiator. It is usually between 30 minutes and 2 hours, preferably between 1 and 2 hours. When the polymerization time is less than 30 minutes, the desired conversion is not reached at times. When it exceeds 2 hours, the molecular weight decreases due to decomposition of polyglycolic acid, and it is sometimes difficult to obtain a monofilament having desired properties.

Although the random copolymer which is an intermediate is amorphous, the random-block copolymer of the present invention has an appropriate crystallinity and an appropriate intrinsic viscosity (index of a molecular weight) which are required for the extrusion-molding in the spinning of the monofilament. The crystallinity of the random-block copolymer is 10% or more according to the X-ray diffraction. After the extrusion-molding, the spinning and the stretching, the resulting monofilament can maintain its structure.

The intrinsic viscosity (its measuring method will be described in Examples later) of the random-block copolymer in the present invention is preferably in the range of from 0.8 to 3 dl/g, especially preferably in the range of from approximately 1 to 2 dl/g at 30° C. When the intrinsic viscosity is less than 0.8 dl/g, the viscosity at the spinning temperature is too low, making it hard to obtain a good-quality filament. When it exceeds 3 dl/g, the spinning becomes hard owing to the high viscosity.

The monofilament of the present invention is produced by spinning and stretching the above-mentioned random-block copolymer. The spinning can be conducted by a known method. This is also the same with the stretching.

When the monofilament is produced through melt-spinning, the spinning temperature is preferably between 200 and 260° C. When it is less than 200° C., the viscosity of the copolymer is too high, and the spinning is difficult. Further, when it exceeds 260° C., the glycolic acid polymer is mainly decomposed, so that the strength of the resulting monofilament is decreased. It is also possible that the random-block copolymer is dissolved in an appropriate solvent to form a solution and this solution is spun. In this case, chloroform, toluene or xylene can be used as a solvent. The concentration of the solution is preferably between 10 and 30% by weight. In this case, the spinning is conducted at a temperature lower than a boiling point of a solvent. The former melt-spinning method is more recommendable than the latter solution-spinning method.

A monofilament having a tensile strength of at least 50,000 psi is obtained by forming an unstretched yarn through spinning and stretching the resulting unstretched yarn. With respect to preferable stretching conditions, the stretching temperature is between 60 and 180° C., and the stretch ratio is between 4 and 15. When the stretch ratio is less than 4, no satisfactory tensile strength is obtained. Meanwhile, when the stretch ratio exceeds 15, the monofilament is broken at times in the stretching, and it is unwanted.

The monofilament which is obtained by the stretching under the above-mentioned conditions is heat-treated at a temperature of at least 80° C. and less than the melting point of the copolymer. The heat treatment temperature is specifically between 80 and 150° C. The heat treatment time is preferably between 1 and 24 hours. Usually, this treatment is conducted, for example, on condition that the monofilament is wound on a bobbin or the like while an appropriate tension is exerted thereon.

The monofilament of the present invention has a tensile strength of at least 50,000 psi, usually at least 60,000 psi. A knot tensile strength reaches at least 30,000, usually at least 40,000. The Young's modulus can be at most 150,000 psi, generally at most 100,000 psi. The elongation can be at most 80%, preferably at most 60%. Further, a monofilament having a diameter of from 4 to 40 mils is provided. The monofilament having such properties can appropriately be used as a bioabsorbable surgical suture.

The random-block copolymer and the monofilament thereof in the present invention have a higher rate of hydrolysis than poly(p-dioxanone) and a monofilament thereof, are more improved in a flexibility and a mechanical strength and have a lower rate of hydrolysis than a random-block copolymer comprising a lactide-glycolide random copolymer segment and a block polymer segment of p-dioxanone and a monofilament thereof or a random-block copolymer comprising an ε-caprolactone-glycolide random copolymer segment and a block polymer segment of glycolide and a monofilament thereof. Accordingly, the random-block copolymer of the present invention can be used as a bioabsorbable surgical suture in the monofilament form, not in the multifilament form.

DESCRIPTION OF THE PREFERRED EMBODIMENTS

The present invention is illustrated specifically by referring to the following Examples. However, the present invention is not limited to these Examples.

The values of the properties described in Examples were measured by the following methods.

1. Amounts of Residual Monomers (% by Weight)

A calibration curve of gas chromatography (163-type Gas Chro Device, manufactured by Hitachi Ltd., capillary column: cp-si 5CB, 50 m×0.32 mm (diameter), column temperature: 170° C.) was prepared using a monomer having a known concentration. Then, 0.3 g of the copolymer obtained were dissolved in 10 ml of hexafluoroisopropanol (hereinafter referred to as "HFIP") to measure amounts of residual monomers.

2. Intrinsic Viscosity (dl/g)

The resulting copolymer (0.100 g) was dissolved in 20 ml of HFIP to prepare 0.5 g/dl of an HFIP solution. A viscosity of the solution was measured at 30° C. using an Ubbellohde (1B type) viscometer, and an intrinsic viscosity (η:dl/g) was calculated using the following equation.

$$\eta = \frac{\ln(t/t_o)}{C}$$

wherein t: falling time [s] of a polymer solution $t_0$: falling time [s] of a solvent C: concentration [g/dl] of a solution 3. Tensile Strength Test (kpsi)

A tensile strength was measured with a chuck width of 100 mm and a crosshead speed of 100 mm/min by a method described in United State Pharmacopoeia, XXIII, (881) using a tensile tester (Tensilon RTA-100, manufactured by Orientech K.K.). With respect to a knot tensile strength, a center of a filament was wound on a flexible rubber tube 6.5 mm in inner diameter and 1.6 mm in thickness to form a surgical knot. Then, the rubber tube was pulled out to give a sample. A Young's modulus was calculated from a gradient of an initial linear elasticity region of the resulting stress-strain curve using the following equation. The unit of the tensile strength and the Young's modulus obtained through measurement is [kg/mm$^2$], but a value calculated in terms of [kpsi] was shows in these Examples.

$$\text{Young's modulus} = (\tan \theta \times L \times C \times S)/(H \times A)$$

wherein

θ: Angle [°] between an initial line and an x-axis (strain axis) in the stress-strain curve L1: Interchuck distance [mm]

C: Chart speed [mm/min]

S: Load per 1 scale of a y-axis (stress axis)

H: Crosshead speed [mm/min]

A: Initial sectional area [mm$^2$] of a filament

EXAMPLE 1

Lactide (140.7 g, hereinafter referred to as "LTD") and 60.4 g of caprolactone (hereinafter referred to as "CL") were charged into a 1-liter reaction flask. Stannous octoate (0.0032 mol % based on the total amount of LTD and CL, 2.0 ml of a solution of 0.1 g of tin octoate in 10 ml of toluene) and 0.14 mol %, based on the total amount of LTD and CL, of lauryl alcohol were added thereto. The reaction flask was allowed to stand at room temperature and a pressure of 140 Pa (1 mmHg) or less for 60 minutes. Subsequently, the pressure was returned to a normal pressure, and the mixture was heated in a nitrogen stream at 140° C. for 20 minutes while being stirred. Further, the polymerization was conducted at 180° C. for 6 hours. The amounts of the residual monomers in the copolymer obtained at this time were 3.7% by weight. Then, 800.2 g of glycolide (hereinafter referred to as "GLD") were added thereto, and the polymerization was conducted at 215° C. for 30 minutes, and further at 235° C. for 1 hour. The amounts of the residual monomers in the copolymer obtained were 4.8% by weight. The intrinsic viscosity (η) was 1.86 dl/g, and the melting point was 224° C.

The resulting copolymer was spun at an extrusion temperature of 240° C. to form a monofilament unstretched yarn. An extruder having a nozzle with a bore diameter of 2.0 mm was used. The resulting unstretched yarn was stretched 8.0 times at a temperature of 120° C., and a tensile strength, a knot tensile strength, an elongation and a Young's modulus of the resulting stretched monofilament were measured. The results are shown in Table 1.

Further, the resulting stretched yarn was heat-treated at 120° C. for 3 hours. A tensile strength, a knot tensile strength, an elongation and a Young's modulus of the heat-treated stretched monofilament are shown in Table 1.

For conducting a hydrolysis test, the heat-treated stretched yarn was dipped in a phosphate buffer solution of 37° C., and a tensile strength retention rate (on Day 20, 30 or 60) and a weight retention rate (on Day 5, 50, 90, 120 or 150) after the lapse of a predetermined period of time were measured. The results obtained are shown in Table 1.

TABLE 1

|  |  | Example | | | | |
|---|---|---|---|---|---|---|
|  |  | 1 | 2 | 3 | 4 | 5 |
| Amount (% wt.) | caprolactone | 14 | 16 | 4 | 21 | 35 |
|  | lactide | 6 | 4 | 16 | 9 | 15 |

TABLE 1-continued

|  |  | Example | | | | |
|---|---|---|---|---|---|---|
|  |  | 1 | 2 | 3 | 4 | 5 |
|  | glycolide | 80* | 80* | 80* | 70* | 50* |
|  | p-dioxanone | — | — | — | — | — |
| Conversion (%) |  | 95.2 | 97 | 95.8 | 96.8 | 95.3 |
| Intrinsic viscosity (dl/g) |  | 1.86 | 1.9 | 2.01 | 1.94 | 1.91 |
| Melting point (° C.) |  | 223 | 224 | 223 | 223 | 222 |
| (Filament) | Diameter (mils) | 9.4 | 9.1 | 9.5 | 9.4 | 9.5 |
| Stretching | Tensile strength (kpsi) | 73 | 69 | 70 | 61 | 57 |
|  | Knot tensile strength (kpsi) | 50 | 49 | 46 | 38 | 31 |
|  | Elongation (%) | 54 | 41 | 57 | 50 | 51 |
|  | Young's modulus | 148 | 131 | 142 | 104 | 83 |
| (Filament) | Temperature (° C.) | 120 | 120 | 120 | 120 | 120 |
| Heat treatment | Time (hr) | 3 | 3 | 3 | 3 | 3 |
|  | Diameter (mils) | 9.4 | 9.0 | 9.1 | 9.1 | 8.8 |
|  | Tensile strength (kpsi) | 73 | 69 | 70 | 61 | 57 |
|  | Knot tensile strength (kpsi) | 50 | 48 | 47 | 38 | 31 |
|  | Elongation (%) | 44 | 35 | 38 | 35 | 32 |
|  | Young's modulus (kpsi) | 152 | 135 | 145 | 111 | 86 |
| Tensile strength | on Day 20 | 73 | 75 | 71 | 70 | 65 |
| retention rate (%) | on Day 30 | 42 | 38 | 31 | 30 | 23 |
|  | on Day 60 | 27 | 25 | 15 | 12 | 8 |
| Weight retention | on Day 5 | 100 | 100 | 100 | 100 | 100 |
| rate (wt. %) | on Day 50 | 87 | 84 | 81 | 77 | 79 |
|  | on Day 90 | 72 | 68 | 62 | 51 | 58 |
|  | on Day 120 | 49 | 42 | 31 | 24 | 27 |
|  | on Day 150 | 28 | 36 | 19 | 18 | 20 |

*indicating a block polymer segment

EXAMPLES 2 TO 5 AND COMPARATIVE EXAMPLES 1 TO 4

The polymerization was conducted in the same manner as in Example 1 except that the amounts of CL, LTD, GLD and PDO were changed as shown in Tables 1 and 2, and spinning, stretching and heat treatment were further conducted in the same manner as in Example 1. The results obtained are shown in said tables. In Comparative Example 4, the amount of glycolide was too small to conduct the spinning.

With respect to the proportions of lactide and caprolactone used to produce the random copolymer in the present invention, it is preferable that lactide is between 20 and 80 mol % while caprolactone is between 80 and 20 mol % (Examples 1 to 3).

When the proportion of lactide is less than 20 mol %, the blocking property of polycaprolactone is increased, and an amorphous lactide-caprolactone copolymer is hardly obtained.

Further, two melting points, 60° C. which is a melting point of polycaprolactone and 225° C. which is a melting point of polyglycolic acid are provided, making it difficult to set stretching conditions and heat treatment conditions. Still further, a heat resistance of the resulting monofilament is decreased, and the product tends to be deformed at a low temperature (Comparative Example 1).

When the proportion of lactide exceeds 80 mol %, a blocking property of polylactic acid is increased, and an amorphous lactide-caprolactone copolymer is hardly obtained. Two melting points, 180° C. which is a melting point of polylactic acid and 225° C. which is a melting point of polyglycolic acid are provided, making it difficult to set stretching conditions and heat treatment conditions. Further, the resulting monofilament has a high strength, but no satisfactory flexibility required for a suture is obtained (Comparative Example 2).

TABLE 2

|  |  | Comparative Examples | | | | | | |
|---|---|---|---|---|---|---|---|---|
|  |  | 1 | 2 | 3 | 4 | 5 | 6 | 7 |
| Amount | caprolactone | 18 | 2 | 3 | 49 | — | — | — |
| (% wt.) | lactide | 2 | 18 | 1 | 21 | 5 | — | — |
|  | glycolide | 80* | 80* | 96* | 30* | 5 | — | — |
|  | p-dioxanone | — | — | — | — | 90* | 100 | — |
| Conversion (%) |  | 96.2 | 96.4 | 96.7 | 96.2 | 89.4 | 87.6 | — |
| Intrinsic viscosity (dl/g) |  | 1.90 | 1.88 | 1.96 | 1.80 | 2.41 | 1.88 | 1.41 |
| Melting point (° C.) |  | 223 | 223 | 225 | 220 | 106 | 109 | 210 |
| (Filament) | Diameter (mils) | 9.1 | 9.4 | 9.1 | Unspin- | 9.5 | 10.1 | 9.4 |
| Stretching | Tensile strength (kpsi) | 43 | 40 | 61 | nable | 65 | 72 | 70 |
|  | Knot tensile strength (kpsi) | 28 | 25 | 31 |  | 54 | 45 | 55 |
|  | Elongation (%) | 58 | 41 | 35 |  | 53 | 51 | 50 |
|  | Young's modulus | 120 | 116 | 410 |  | 155 | 315 | 127 |
| (Filament) | Temperature (° C.) | — | 120 | 120 | Unspin- | 80 | 60 | — |

TABLE 2-continued

|  |  | \multicolumn{7}{c}{Comparative Examples} |
| --- | --- | --- | --- | --- | --- | --- | --- | --- |
|  |  | 1 | 2 | 3 | 4 | 5 | 6 | 7 |
| Heat treatment | Time (hr) | — | 3 | 3 | nable | 6 | 12 | — |
|  | Diameter (mils) | 9.4 | 9.4 | 9.4 |  | 9.5 | 10.3 | 9.4 |
|  | Tensile strength (kpsi) | 47 | 51 | 63 |  | 67 | 74 | 75 |
|  | Knot tensile strength (kpsi) | 33 | 36 | 44 |  | 58 | 55 | 61 |
|  | Elongation (%) | 42 | 33 | 21 |  | 37 | 29 | 30 |
|  | Young's modulus | 141 | 132 | 415 |  | 162 | 324 | 130 |
| Tensile strength retention rate (%) | on Day 20 | 71 | 67 | 70 | Unmeas- | 40 | 70 | 41 |
|  | on Day 30 | 30 | 31 | 28 | urable | 12 | 50 | 11 |
|  | on Day 60 | 12 | 9 | 10 |  | 0 | 40 | 0 |
| Weight retention rate (wt. %) | on Day 5 | 100 | 100 | 100 |  | 100 | 100 | 100 |
|  | on Day 50 | 94 | 94 | 92 |  | 64 | 94 | 59 |
|  | on Day 90 | 84 | 81 | 71 |  | 36 | 83 | 23 |
|  | on Day 120 | 61 | 58 | 50 |  | 0 | 78 | 0 |
|  | on Day 150 | 42 | 39 | 30 |  | 0 | 73 | 0 |

*indicating a block polymer segment

In the present invention, from 5 to 50 mol % of the above-obtained lactide-caprolactone random copolymer and from 95 to 50 mol % of glycolide are used. Preferably, from 10 to 30 mol % of the lactide-caprolactone random copolymer and from 90 to 70 mol % of glycolide are used. When the random copolymer is less than 5 mol %, a satisfactory flexibility is hardly obtained (Comparative Example 3).

When the random copolymer exceeds 50 mol %, a monofilament which is flexible but has a satisfactory strength is not obtained (Examples 4 and 5, and Comparative Example 4).

COMPARATIVE EXAMPLE 5

LTD (50.3 g) and 50.6 g of GLD were charged into a 1-liter reaction flask, and 0.0032 mol %, based on the total amount of LTD and GLD, of stannous octoate (2.0 ml of a solution of 0.05 g of stannous octoate in 10 ml of toluene) and 0.14 mol %, based on the total amount of LTD and GLD, of lauryl alcohol were added thereto. The reaction flask was allowed to stand at room temperature and a pressure of 140 Pa (1 mmHg) or less for 60 minutes. Subsequently, the pressure was returned to a normal pressure, and the mixture was heated in a nitrogen stream at 140° C. for 20 minutes while being stirred. Further, the polymerization was conducted at 200° C. for 3 hours. The amounts of the residual monomers in the copolymer obtained were 2.4% by weight. Then, 900.4 g of p-dioxanone (hereinafter referred to as "PDO") were added thereto, and the polymerization was conducted at 110° C. for 8 hours. The amounts of the residual monomers in the copolymer obtained were 11.6% by weight. The intrinsic viscosity ($\eta$) was 2.41 dl/g, and the melting point was 106° C.

The resulting copolymer was spun at an extrusion temperature of 120° C. to form a monofilament unstretched yarn. An extruder having a nozzle with a bore diameter of 2.0 mm was used. The resulting unstretched yarn was stretched 8 times at a stretching temperature of 80° C. A tensile strength, a knot tensile strength, an elongation and a Young's modulus of the resulting stretched yarn are shown in Table 2.

Further, the resulting stretched yarn was heat-treated at 80° C. for 6 hours. A tensile strength, a knot tensile strength, an elongation and a Young's modulus of the heat-treated stretched yarn were measured. The results are shown in Table 2.

A hydrolysis test of the heat-treated stretched yarn was conducted in the same manner as in Example 1. The results are shown in Table 2.

COMPARATIVE EXAMPLE 6

PDO (1,000.9 g) was charged into a 1-liter reaction flask, and 0.0032 mol %, based on the amount of PDO, of stannous octoate (2.0 ml of a solution of 0.635 g of tin octoate in 10 ml of toluene) and 0.14 mol %, based on the amount of PDO, of lauryl alcohol were added thereto. The reaction flask was allowed to stand at room temperature and a pressure of 1 mmHg or less for 60 minutes. Subsequently, the pressure was returned to a normal pressure, and the mixture was heated in a nitrogen stream at 70° C. for 20 minutes while being stirred. Further, the polymerization was conducted at 110° C. for 8 hours. The amounts of the residual monomers in the polymer were 10.4% by weight. The intrinsic viscosity was 1.88 dl/g, and the melting point was 109° C.

The resulting polymer was treated in the same manner as in Comparative Example 5 except that after the stretching, the resulting product was heat-treated at 60° C. for 12 hours. The results are shown in Table 2.

COMPARATIVE EXAMPLE 7

With respect to Monocryl (trade name for a product of Ethicon Inc., which is produced from a random-block copolymer of ε-caprolactone and glycolide), a commercial suture, the properties were evaluated as in Example 1. The results are shown in Table 2.

What is claimed is:

1. A monofilament which is formed by spinning and stretching a random-block copolymer comprising from 5 to 50 mol % of a random copolymer segment containing from 20 to 80 mol % of a lactide unit (A) and from 80 to 20 mol % of a caprolactone unit (B), and from 95 to 50 mol % of a block copolymer segment containing a glycolide unit (C), wherein the monofilament has a thickness of from 4 to 40 mils, a tensile strength of at least 50,000 psi, a knot tensile strength of at least 30,000 psi and a Young's modulus of at most 150,000.

2. The monofilament of claim 1, wherein the intrinsic viscosity of the random-block copolymer is between 0.8 and 3 dl/g.

3. The monofilament of claim 2 which is a surgical suture.

4. The monofilament of claim 1 which is a surgical suture.

5. A surgical suture formed by spinning and stretching a random-block copolymer comprising from 5 to 50 mol % of a random copolymer segment containing from 20 to 80 mol % of a lactide unit (A) and from 80 to 20 mol % of a caprolactone unit (B), and from 95 to 50 mol % of a block copolymer segment containing a glycolide unit (C).

6. The surgical suture of claim 5, wherein the intrinsic viscosity of the random-block copolymer is between 0.8 and 3 dl/g.

* * * * *